(12) United States Patent
Yous et al.

(10) Patent No.: US 7,947,852 B2
(45) Date of Patent: May 24, 2011

(54) NAPHTHALENE COMPOUNDS, A PROCESS FOR THEIR PREPARATION AND PHARMACEUTICAL COMPOSITIONS CONTAINING THEM

(75) Inventors: Said Yous, Loos (FR); Mohamed Ettaoussi, Lille (FR); Ahmed Sabaouni, Armentieres (FR); Pascal Berthelot, Habourdin (FR); Michael Spedding, Le Vesinet (FR); Philippe Delagrange, Issy les Moulineaux (FR); Daniel-Henri Caignard, Boisemont (FR); Mark Millan, Le Pecq (FR)

(73) Assignee: Les Laboratoires Servier, Suresnes Cedex (FR)

( * ) Notice: Subject to any disclaimer, the term of this patent is extended or adjusted under 35 U.S.C. 154(b) by 0 days.

(21) Appl. No.: 12/452,429

(22) PCT Filed: Jul. 1, 2008

(86) PCT No.: PCT/FR2008/000932
§ 371 (c)(1),
(2), (4) Date: Mar. 8, 2010

(87) PCT Pub. No.: WO2009/022063
PCT Pub. Date: Feb. 19, 2009

(65) Prior Publication Data
US 2010/0168244 A1 Jul. 1, 2010

(30) Foreign Application Priority Data

Jul. 2, 2007 (FR) .................................. 07 04747

(51) Int. Cl.
C07C 233/233 (2006.01)
A61K 31/16 (2006.01)

(52) U.S. Cl. ........ 564/219; 564/185; 564/189; 564/190; 564/212; 514/617; 514/624; 514/626; 514/628; 514/630

(58) Field of Classification Search .................. 564/185, 564/189, 190, 212, 219; 514/617, 624, 626, 514/628, 630
See application file for complete search history.

(56) References Cited

U.S. PATENT DOCUMENTS 5,420,158 A * 5/1995 Yous et al. ................... 514/510

FOREIGN PATENT DOCUMENTS

EP 0562956 9/1993

OTHER PUBLICATIONS

Carter et al., Chemotherapy of Cancer, second edition, John Wiley & Sons, N.Y., N.Y., 1981, pp. 362-365.*
International Search Report for PCT/FR2008/00932 of Feb. 9, 2009.
Marot, C., et al., "Pharmacophoric search and 3D-QSAR comparative molecular field analysis studies on agonists of melatonin sheep receptors" Journal of Medicnal Chemistry, vol. 41, No. 23, p. 4453-4465, 1998.
Li, et al., *Drugs of the Future*, 2000, 25, 945-957.
Krause, et al., *Society for Neuroscience*, 1996, 22, No. 651.19, p. 1400.
Vacas, et al., *J. Pineal Research*, 1992, 13, 60-65.
Cagnacci, et al., *J. Pineal Research*, 1997, 22, 16-19.
Lagneux, et al., *Life Sciences*, 2000, 66, 503-509.
Brydon, et al., *Endocrinology*, 2001, 142, 4264-4271.
Bylesjö, et al., *International Journal of Eating Disorders*, 1996, 20, 443-446.
Ferrari, et al., *Biol. Psychiatry*, 1990, 27, 1007-1020.
Mazzucchelli, et al., *Molecular Brain Research*, 1996, 39, 117-126.
Brown, *CNS Drugs*, 1995, 3, 209-226.
Waldhauser, et al., *Psychopharmacology*, 1990, 100, 222-226.
Skene, et al., *Brain Research*, 1990, 528, 170-174.
Monteleone, et al., *Schizophrenia Research*, 1992, 7, 77-84.
McIntyre, et al., *Journal of Affective Disorders*, 1987, 12, 203-206.
Erlich, et al., *J. Neurosurg.*, 1985, 63, 321-341.
Maurizi, *Medical Hypotheses*, 1988, 27, 271-276.
Kopp, et al., *Behavioural Pharmacology*, 1999, 10, 73-83.
Kopp, et al., *Neuorpharmacology*, 2000, 39, 1865-1871.
Fanteck, et al., *Exp. Brain Res.*, 1995, 107, 321-325.
Rasmussen, et al., *Endocrinology*, 1999, 140, 1009-1012.
Armstrong, et al., *Medical Hypotheses*, 1991, 34, 300-309.
O'Brien, et al., *Clinical Endocrinology*, 1986, 24, 359-364.
Motilva, et al., *Current Pharmaceutical Design*, 2001, 7, 909-931.
Tamarkin, et al., *Science*, 1985, 227, 714-720.
Chemineau, et al., *Rec. Med. Vet.*, 1991, 167, 227-239.
Xu, et al., *Drug Development Research*, 1996, 39, 167-173.
Régrigny, et al., *Am. J. Physiol.*, 1998, 275, 139-144.
Stankov, et al., *Neuroscience*, 1993, 52, 459-468. Leone, et al., *Cephalalgia*, 1996, 16, 494-496.
Brun, et al., *Cephalalgia*, 1995, 15, 136-139.
Ying, et al., *Eur. J. of Pharmacology*, 1993, 246, 89-96.
Laudon, et al., *Journal of Clinical Endocrinology and Metabolism*, 1996, 81, 1336-1342.
Lissoni, et al., *British Journal of Cancer*, 1996, 74, 1466-1468.

* cited by examiner

*Primary Examiner* — Shailendra Kumar
(74) *Attorney, Agent, or Firm* — Hueschen and Sage

(57) ABSTRACT

Compounds of formula (I):

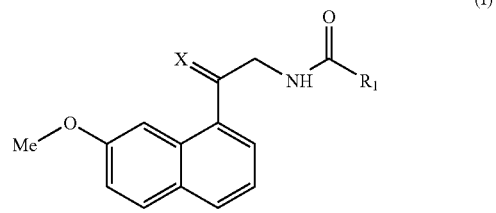

wherein:
$R_1$ represents alkyl, alkenyl, haloalkyl, polyhaloalkyl, cycloalkyl, cycloalkylalkyl, aryl, arylalkyl, heteroaryl or heteroarylalkyl,
X represents a group $N-OR_2$ wherein $R_2$ represents a hydrogen atom or an alkyl group.
Medicinal products containing the same which are useful in treating disorders of the melatoninergic system.

7 Claims, No Drawings

NAPHTHALENE COMPOUNDS, A PROCESS FOR THEIR PREPARATION AND PHARMACEUTICAL COMPOSITIONS CONTAINING THEM

The present invention relates to new naphthalene compounds, to a process for their preparation and to pharmaceutical compositions containing them.

The compounds of the present invention are new and have very valuable pharmacological characteristics relating to melatoninergic receptors.

Numerous studies in the last ten years have demonstrated the key role of melatonin (N-acetyl-5-methoxytryptamine) in many physiopathological phenomena and in the control of circadian rhythms. Its half-life is quite short, however, owing to the fact that it is rapidly metabolised. Great interest therefore lies in the possibility of providing the clinician with melatonin analogues that are metabolically more stable, that have an agonist or antagonist character and that may be expected to have a therapeutic effect that is superior to that of the hormone itself.

In addition to their beneficial action on circadian rhythm disorders (J. Neurosurg. 1985, 63, pp. 321-341) and sleep disorders (Psychopharmacology, 1990, 100, pp. 222-226), ligands of the melatoninergic system have valuable pharmacological properties in respect of the central nervous system, especially anxiolytic and antipsychotic properties (Neuropharmacology of Pineal Secretions, 1990, 8 (3-4), pp. 264-272) and analgesic properties (Pharmacopsychiat., 1987, 20, pp. 222-223) as well as for the treatment of Parkinson's disease (J. Neurosurg. 1985, 63, pp. 321-341) and Alzheimer's disease (Brain Research, 1990, 528, pp. 170-174). Those compounds have also demonstrated activity in respect of certain cancers (Melatonin—Clinical Perspectives, Oxford University Press, 1988, pp. 164-165), ovulation (Science 1987, 227, pp. 714-720), diabetes (Clinical Endocrinology, 1986, 24, pp. 359-364), and in the treatment of obesity (International Journal of Eating Disorders, 1996, 20 (4), pp. 443-446).

Those various effects are exerted via the intermediary of specific melatonin receptors. Molecular biology studies have demonstrated the existence of a number of receptor sub-types that are capable of binding that hormone (Trends Pharmacol. Sci., 1995, 16, p. 50; WO 97.04094). For various species, including mammals, it has been possible for some of those receptors to be located and characterised. In order to be able to understand the physiological functions of those receptors better, it is of great advantage to have available selective ligands. Moreover, such compounds, by interacting selectively with one or other of those receptors, may be excellent medicaments for the clinician in the treatment of pathologies associated with the melatoninergic system, some of which have been mentioned above.

Besides the fact that they are new, the compounds of the present invention exhibit a very strong affinity for melatonin receptors.

They moreover have a strong affinity for the 5-HT$_{2C}$ receptor, which has the effect of reinforcing the properties observed in the case of melatoninergic receptors, especially in the field of depression.

More specifically, the present invention relates to the compounds of formula (I):

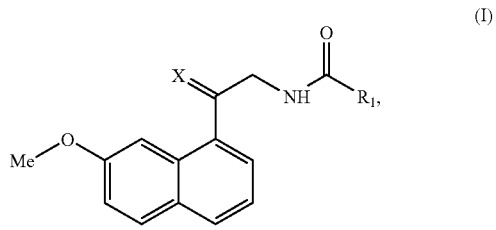

wherein:
$R_1$ represents a linear or branched $(C_1-C_6)$alkyl group, a linear or branched $(C_1-C_6)$alkenyl group, a linear or branched $(C_1-C_6)$haloalkyl group, a linear or branched $(C_1-C_6)$polyhaloalkyl group, a $(C_3-C_8)$cycloalkyl group, a $(C_3-C_8)$cycloalkyl-$(C_1-C_6)$alkyl group in which the alkyl moiety may be linear or branched, an aryl group, an aryl-$(C_1-C_6)$alkyl group in which the alkyl moiety may be linear or branched, a heteroaryl group or a heteroaryl-$(C_1-C_6)$alkyl group in which the alkyl moiety may be linear or branched, X represents a group N—OR$_2$ wherein R$_2$ represents a hydrogen atom or a linear or branched $(C_1-C_6)$alkyl group, it being understood that:
the oxime =N—OR$_2$ may be of Z or E configuration,
"aryl" means a phenyl, naphthyl or biphenyl group,
"heteroaryl" means any mono- or bi-cyclic aromatic group containing from 1 to 3 hetero atoms selected from oxygen, sulphur and nitrogen,
it being possible for the aryl and heteroaryl groups so defined to be substituted by from 1 to 3 groups selected from linear or branched $(C_1-C_6)$alkyl, linear or branched $(C_1-C_6)$alkoxy, hydroxy, carboxy, formyl, nitro, cyano, linear or branched $(C_1-C_6)$haloalkyl, linear or branched $(C_1-C_6)$polyhaloalkyl, alkyloxycarbonyl and halogen atoms,
to their enantiomers and diastereoisomers, and also to addition salts thereof with a pharmaceutically acceptable acid or base.

Among the pharmaceutically acceptable acids there may be mentioned by way of non-limiting example hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, camphoric acid etc.

Among the pharmaceutically acceptable bases there may be mentioned by way of non-limiting example sodium hydroxide, potassium hydroxide, triethylamine, tert-butylamine etc.

Preferred compounds of the invention are compounds of formula (I) wherein R$_1$ represents a linear or branched $(C_1-C_6)$alkyl group such as, for example, a methyl group.

The R$_2$ group advantageously represents a hydrogen atom or a methyl group.

The invention even more specifically relates to the compounds which are N-[(2E)-2-(hydroxyimino)-2-(7-methoxy-1-naphthyl)ethyl]acetamide, N-[(2Z)-2-(hydroxyimino)-2-(7-methoxy-1-naphthyl)ethyl]acetamide and N-[(2E)-2-(methoxyimino)-2-(7-methoxy-1-naphthyl)ethyl]acetamide.

The addition salts of preferred compounds of the invention with a pharmaceutically acceptable acid or base form an integral part of the invention.

The invention relates also to a process for the preparation of the compound of formula (I), which process is characterised in that there is used as starting material the compound of formula (II):

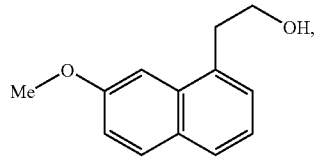

which is subjected to the action of mesyl chloride to yield the compound of formula (III):

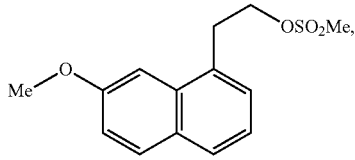

which is placed in a basic medium to yield the compound of formula (IV):

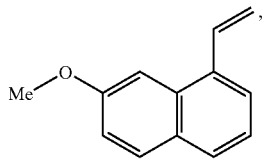

which is subjected to oxidation to yield the compound of formula (V):

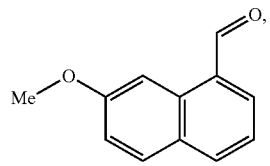

which is subjected to the action of trimethylsilyl cyanide to yield the compound of formula (VI):

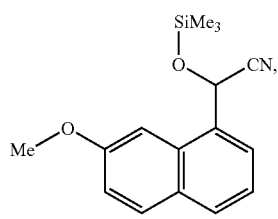

which is subjected to reduction to yield the compound of formula (VII):

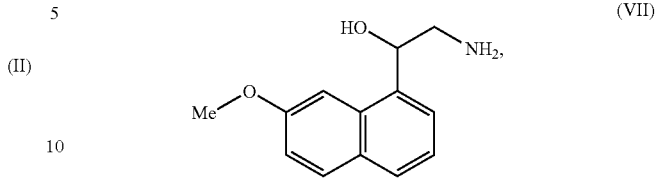

which is subjected to the action of the compound of formula $R_1COCl$, wherein $R_1$ is as defined for formula (I), to yield the compound of formula (VIII):

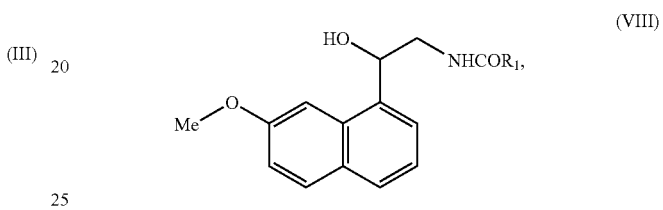

wherein $R_1$ is as defined hereinbefore,
which is subjected to the action of potassium chlorochromate to yield the compound of formula (IX):

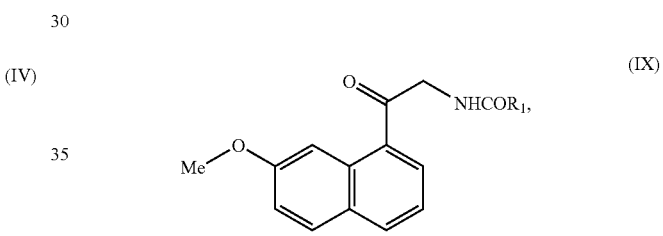

wherein $R_1$ is as defined hereinbefore,
with which there is condensed the compound of formula $R_2O—NH_2$, wherein $R_2$ is as defined for formula (I), to yield the compound of formula (I), which may be purified according to a conventional separation technique, which is converted, if desired, into its addition salts with a pharmaceutically acceptable acid or base, and which is separated, where appropriate, into its isomers according to a conventional separation technique.

The compound of formula (II) can be obtained by the person skilled in the art using conventional chemical reactions described in the literature.

Pharmacological study of the compounds of the invention has shown them to be atoxic, to have strong selective affinity for melatonin receptors and to have significant activities in respect of the central nervous system; and, in particular, there have been found therapeutic properties in respect of sleep disorders, antidepressive, anxiolytic, antipsychotic and analgesic properties and properties in respect of microcirculation, enabling it to be established that the compounds of the invention are useful in the treatment of stress, sleep disorders, anxiety, seasonal affective disorder or major depression, cardiovascular pathologies, pathologies of the digestive system, insomnia and fatigue due to jetlag, schizophrenia, panic attacks, melancholia, appetite disorders, obesity, insomnia, psychotic disorders, epilepsy, diabetes, Parkinson's disease, senile dementia, various disorders associated with normal or pathological ageing, migraine, memory loss and Alzheimer's disease, and in cerebral circulation disorders. In another field of activity, it appears that, in treatment, the compounds of the invention can be used in sexual dysfunctions, that they have ovulation-inhibiting and immunomodulating properties and that they may potentially be used in the treatment of cancers.

The compounds will preferably be used in the treatment of major depression, seasonal affective disorder, sleep disorders; cardiovascular pathologies, pathologies of the digestive system, insomnia and fatigue due to jetlag, appetite disorders and obesity.

For example, the compounds will be used in the treatment of major depression, seasonal affective disorder and sleep disorders.

The present invention relates also to pharmaceutical compositions comprising at least one compound of formula (I) on its own or in combination with one or more pharmaceutically acceptable excipients.

Among the pharmaceutical compositions according to the invention there may be mentioned more especially those that are suitable for oral, parenteral, nasal, per- or transcutaneous, rectal, perlingual, ocular or respiratory administration and especially tablets or dragées, sublingual tablets, sachets, paquets, capsules, glossettes, lozenges, suppositories, creams, ointments, dermal gels, and drinkable or injectable ampoules.

The dosage varies according to the sex, age and weight of the patient, the route of administration, the nature of the therapeutic indication or any associated treatments and ranges from 0.01 mg to 1 g per 24 hours in one or more administrations.

The following Examples illustrate the invention but do not limit it in any way.

EXAMPLE 1

N-[(2Z)-2-(Hydroxyimino)-2-(7-methoxy-1-naphthyl)ethyl]acetamide

Step A: 2-(7-Methoxy-1-naphthyl)ethyl methanesulphonate 2-(7-Methoxy-1-naphthyl)ethanol (25 mmol) and triethylamine (30 mmol) are dissolved in 50 ml of dichloromethane and the reaction mixture is cooled to 0° C. using an ice bath. Mesyl chloride (30 mmol) is added dropwise and the reaction mixture is stirred at ambient temperature for 2 hours and then poured into 100 ml of water. The organic phase is washed with 1M hydrochloric acid solution and then with water, dried over magnesium sulphate and evaporated. The oil obtained is precipitated from a mixture of diethyl ether/petroleum ether (1/1). The title product is filtered off under suction and then recrystallised from to diisopropyl ether.
Melting point: 60-62° C.

Step B: 7-Methoxy-1-vinylnaphthalene

The compound obtained in Step A (21.4 mmol) is dissolved in 120 ml of tetrahydrofuran, and potassium tent-butylate (64.2 mmol) is added in small portions. After stirring for 30 minutes at ambient temperature, the reaction mixture is evaporated to dryness. The residue obtained is taken up in 150 ml of water and the aqueous phase is extracted twice with 60 ml of diethyl ether. The organic phase is washed with water, dried over magnesium sulphate, decolourised on vegetable carbon and evaporated. The residue obtained is purified on silica gel (eluant: petroleum ether) to yield the title product in the form of a yellow oil.

Step C: 7-Methoxy-1-naphthaldehyde

The compound obtained in Step B (13.4 mmol) and osmium tetroxide (0.16 mmol) are dissolved in 70 ml of a mixture of tetrahydrofuran/water (1/1). Sodium periodate (26.9 mmol) is added in small portions and the reaction mixture is stirred for 2 hours at ambient temperature. The reaction mixture is poured into 50 ml of 5% sodium hydrogen carbonate solution, the insoluble material is filtered off and the aqueous phase is extracted twice with 75 ml of ether. The organic phase is washed with water, decolourised and evaporated. The precipitate obtained is recrystallised from cyclohexane and yields the title product in the form of a white solid.
Melting point: 61-63° C.

Step D: (7-Methoxy-1-naphthyl)[(trimethylsilyl)oxy]acetonitrile

Methyltriphenylphosphonium iodide (5.7 mmol) is dissolved in 250 ml of anhydrous dichloromethane, under argon, and then trimethylsilyl cyanide (170.8 mmol) and the compound obtained in Step C (56.9 mmol) are added. The reaction mixture is stirred at ambient temperature for 72 hours and then 200 ml of water are added. The two phases are separated and the aqueous phase is extracted with 50 ml of dichloromethane. The organic phases are collected, dried over magnesium sulphate and evaporated under reduced pressure. The precipitate is filtered off from ether under suction and recrystallised from cyclohexane to yield the title product in the form of a white solid.
Melting point: 123-125° C.

Step E: 2-Amino-1-(7-methoxy-1-naphthyl)ethanol hydrochloride

In a three-necked flask under argon, lithium aluminium hydride (37.1 mmol) is suspended in 200 ml of diethyl ether. The compound obtained, in Step D (18.6 mmol), dissolved in 50 ml of tetrahydrofuran, is added dropwise. The reaction mixture is stirred at ambient temperature for 1 hour. The excess of lithium aluminium hydride is destroyed by successive additions of 1.4 ml of water, 1.4 ml of 15% sodium hydroxide and 4.2 ml of water. The inorganic precipitate formed is removed by filtration and washed with 50 ml of tetrahydrofuran. The filtrate is dried over magnesium sulphate and evaporated under reduced pressure. The oil obtained is dissolved in 100 ml of diethyl ether and treated with diethyl ether saturated with gaseous HCl. The diethyl ether is evaporated off under reduced pressure, and the solid obtained is filtered off under suction and recrystallised from acetonitrile to yield the title product in the form of a white solid.
Melting point: 207-209° C.

Step F: N-[2-Hydroxy-2-(7-methoxy-1-naphthyl)ethyl]acetamide

The compound obtained in Step E (20 mmol) is dissolved in a mixture of water/ethyl acetate (25 ml/75 ml) cooled to 0° C. Potassium carbonate (60 mmol) is added, and then acetyl chloride (26 mmol) is added dropwise to the reaction mixture. The mixture is stirred vigorously for 30 minutes at ambient temperature. The two phases are separated and the organic phase is washed with 0.1M aqueous hydrochloric acid solution and then with water. After drying over magnesium sulphate, the organic phase is evaporated under reduced pressure. The residue obtained is recrystallised from acetonitrile to yield the title product in the form of a white solid.
Melting point: 173-175° C.

Step G:
N-[2-(7-Methoxy-1-naphthyl)-2-oxoethyl]acetamide

The compound obtained in Step F (7.7 mmol) is dissolved in 200 ml of anhydrous dichloromethane. The resulting solution is added to a suspension of potassium acetate (0.23 g) and pyridinium chlorochromate (11.6 mmol) in 50 ml of dichloromethane. The reaction mixture is stirred at ambient temperature for 2 hours. It is then filtered over Celite. The filtrate is washed with water, decolourised on vegetable carbon and evaporated under reduced pressure. The residue obtained is triturated in diethyl ether, filtered off under suction and recrystallised from diisopropyl ether to yield the title product in the form of a white solid.
Melting point: 122-124° C.

Step H: N-[(2Z)-2-(Hydroxyimino)-2-(7-methoxy-1-naphthyl)ethyl]acetamide

In a 100-ml round-bottom flask, the compound obtained in Step G (4.2 mmol) is dissolved in 25 ml of methanol. Hydroxylamine hydrochloride (16.8 mmol) and pyridine (21.1 mmol) are added and then the reaction mixture is heated at reflux, with magnetic stirring, for 3 hours. After cooling, the reaction mixture is poured into 50 ml of water. The precipitate formed is filtered off under suction, washed with water and recrystallised from toluene to yield the title product in the form of a white solid.
Melting point: 136-138° C.

EXAMPLE 2

N-[(2E)-2-(Hydroxyimino)-2-(7-methoxy-1-naphthyl)ethyl]acetamide

The procedure is as in Example 1. The precipitate formed in Step H is filtered off under suction, washed with water and recrystallised from acetonitrile to yield the title product in the form of a white solid.
Melting point: 157-159° C.
Elemental microanalysis:

| % | C | H | N |
|---|---|---|---|
| Calculated: | 66.16 | 5.92 | 10.29 |
| Found: | 65.93 | 5.85 | 10.21 |

EXAMPLE 3

N-[(2E)-2-(Methoxyimino)-2-(7-methoxy-1-naphthyl)ethyl]acetamide

The procedure is as in Example 1, replacing the hydroxylamine hydrochloride in Step H with O-methylhydroxylamine hydrochloride. The title product, recrystallised from diisopropyl ether, is obtained in the form of a white solid.
Melting point: 110-112° C.

Elemental microanalysis:

| % | C | H | N |
|---|---|---|---|
| Calculated: | 67.12 | 6.34 | 9.78 |
| Found: | 67.11 | 6.34 | 9.53 |

Pharmacological Study

EXAMPLE A

Acute Toxicity Study

The acute toxicity was evaluated after oral administration to groups each comprising 8 mice (26±2 g). The animals were observed at regular intervals during the course of the first day, and daily for the two weeks following treatment. The $LD_{50}$ (dose that causes the death of 50% of the animals) was evaluated and demonstrated the low toxicity of the compounds of the invention.

EXAMPLE B

Forced Swimming Test

The compounds of the invention are tested in a behavioural model, the forced swimming test.
The apparatus is composed of a plexiglass cylinder filled with water. The animals are tested individually for a session of 6 minutes. At the start of each test, the animal is placed in the centre of the cylinder. The time spent immobile is recorded. The animal is considered to be immobile when it stops struggling and remains immobile on the surface of the water, making only those movements which allow it to keep its head above water.
Following administration 40 minutes before the start of the test, the compounds of the invention significantly reduce the time spent immobile, which indicates their antidepressant activity.

EXAMPLE C

Melatonin $MT_1$ and $MT_2$ Receptor for Binding Study

The $MT_1$ or $MT_2$ receptor binding experiments are carried out using 2-[$^{125}$I]-iodomelatonin as reference radioligand. The radioactivity retained is determined using a liquid scintillation counter.
Competitive binding experiments are then carried out in triplicate using the various test compounds. A range of different concentrations is tested for each compound. The results enable the binding affinities of the compounds tested ($K_i$) to be determined.
The $K_i$ values found for the compounds of the invention accordingly demonstrate binding to one or other of the melatoninergic binding sites, those values being $\leq 10$ µM.
By way of example, the compound obtained in Example 2 has a $K_i(MT_1)$ of 7 nM and a $K_i(MT_2)$ of 0.8 nM.

EXAMPLE D

Serotoninergic $5-HT_{2C}$ Receptor Binding Study

The affinity of the compounds for the human $5-HT_{2C}$ receptor is evaluated on membrane preparations from CHO cells stably expressing that receptor.

Incubation is carried out in 50 mM TRIS buffer, pH 7.4, containing 10 mM $MgCl_2$ and 0.1% BSA, in the presence of [$^3$H]-mesulergine (1 nM) and 25 fmol/ml of receptor. Non-specific binding is determined in the presence of 10 μM mianserin.

The reaction is stopped by the addition of 50 mM TRIS buffer, pH 7.4, followed by a filtration step and 3 successive rinses: the radioactivity bound to the membranes remaining on the filters (GF/B pretreated with 0.1% PEI) is determined by liquid scintillation counting.

The results obtained show that the compounds of the invention have affinity for the 5-$HT_{2C}$ receptor, with $K_i$ values <10 μM.

EXAMPLE E

Action of the Compounds of the Invention on the Circadian Rhythms of Locomotor Activity of the Rat The involvement of melatonin in the entrainment, by day/night alternation, of the majority of physiological, biochemical and behavioural circadian rhythms has made it possible to establish a pharmacological model for use in the search for melatoninergic ligands.

The effects of the compounds are tested on numerous parameters and, in particular, on the circadian rhythms of locomotor activity, which are a reliable indicator of the activity of the endogenous circadian clock.

In this study, the effects of such compounds on a particular experimental model, namely the rat placed in temporal isolation (permanent darkness), are evaluated.

Experiment Protocol

One-month-old male rats are subjected, as soon as they arrive at the laboratory, to a light cycle of 12 hours' light per 24 hours (LD 12:12).

After 2 to 3 weeks' adaptation, they are placed in cages fitted with a wheel connected to a recording system, in order to detect the phases of locomotor activity and thus monitor the nychthemeral rhythms (LD) or circadian rhythms (DD).

As soon as the rhythms recorded show stable entrainment by the light cycle LD 12:12, the rats are placed in permanent darkness (DD).

Two to three weeks later, when free running (rhythm reflecting that of the endogenous clock) is clearly established, the rats are given a daily administration of the compound to be tested.

The observations are made by means of visualisation of the rhythms of activity:
 entrainment of the activity rhythms by the light rhythm,
 disappearance of entrainment of the rhythms in permanent darkness,
 entrainment by the daily administration of the compound; transitory or durable effect.

A software package makes it possible:
 to measure the duration and intensity of the activity, the period of the rhythm of the animals in the free-running state and during treatment,
 to demonstrate by spectral analysis the existence of circadian and non-circadian (for example ultradian) components, where present.

Results

The compounds of the invention clearly appear to allow powerful action on the circadian rhythm via the melatoninergic system.

EXAMPLE F

Light/Dark Cages Test

The compounds of the invention are tested in a behavioural model, the light/dark cages test, which allows the anxiolytic activity of the compounds to be demonstrated.

The apparatus consists of two polyvinyl boxes covered with plexiglass. One of the boxes is in darkness. A lamp is placed above the other box, yielding a light intensity of approximately 4000 lux in the centre of the box. An opaque plastic tunnel separates the light box from the dark box. The animals are tested individually for a session of 5 minutes. The floor of each box is cleaned between each session. At the start of each test, the mouse is placed in the tunnel, facing the dark box. The time spent by the mouse in the illuminated box and the number of passages through the tunnel are recorded after the first entry into the dark box.

Following administration of the compounds 30 minutes before the start of the test, the compounds of the invention significantly increase the time spent in the illuminated cage and the number of passages through the tunnel, which demonstrates the anxiolytic activity of the compounds of the invention.

EXAMPLE G

Pharmaceutical Composition: Tablets

| | |
|---|---|
| 1000 tablets each containing a dose of 5 mg of N-[(2E)-2-(hydroxyimino)-2-(7-methoxy-1-naphthyl)ethyl]acetamide (Example 2) | 5 g |
| Wheat starch | 20 g |
| Maize starch | 20 g |
| Lactose | 30 g |
| Magnesium stearate | 2 g |
| Silica | 1 g |
| Hydroxypropylcellulose | 2 g |

The invention claimed is:
1. A compound selected from those of formula (I):

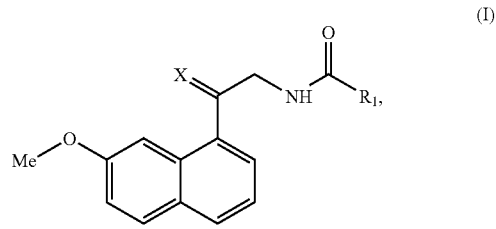

wherein:
$R_1$ represents a linear or branched ($C_1$-$C_6$)alkyl group, a linear or branched ($C_1$-$C_6$)alkenyl group, a linear or branched ($C_1$-$C_6$)haloalkyl group, a linear or branched ($C_1$-$C_6$)polyhaloalkyl group, a ($C_3$-$C_8$)cycloalkyl group, a ($C_3$-$C_8$)cycloalkyl-($C_1$-$C_6$)alkyl group in which the alkyl moiety may be linear or branched, an aryl group, an aryl-($C_1$-$C_6$)alkyl group in which the alkyl moiety may be linear or branched, a heteroaryl group or a heteroaryl-($C_1$-$C_6$)alkyl group in which the alkyl moiety may be linear or branched,
X represents a N—$OR_2$ group wherein $R_2$ represents a hydrogen atom or a linear or branched ($C_1$-$C_6$)alkyl group, it being understood that:
the oxime =N—OR$_2$ may be of Z or E configuration,
"aryl" means phenyl, naphthyl or biphenyl,
"heteroaryl" means a mono- or bi-cyclic aromatic group having from 1 to 3 hetero atoms selected from oxygen, sulphur and nitrogen, wherein the aryl and heteroaryl groups may be optionally substituted by 1 to 3 groups selected from linear or branched (C$_1$-C$_6$)alkyl, linear or branched (C$_1$-C$_6$)alkoxy, hydroxy, carboxy, formyl, nitro, cyano, linear or branched (C$_1$-C$_6$)haloalkyl, linear or branched (C$_1$-C$_6$)polyhaloalkyl, alkyloxycarbonyl and halogen, and enantiomers, diastereoisomers, and addition salts thereof with a pharmaceutically acceptable acid or base.

2. The compound of claim 1, wherein R$_1$ represents a linear or branched (C$_1$-C$_6$)alkyl group.

3. The compound of claim 1, wherein R$_2$ represents a methyl group.

4. The compound of claim 1, wherein R$_2$ represents a hydrogen atom.

5. The compound of claim 1, which is N-[(2E)-2-(hydroxyimino)-2-(7-methoxy-1-naphthyl)ethyl]acetamide, or an addition salt thereof with a pharmaceutically acceptable base.

6. A pharmaceutical composition comprising at least one compound of claim 1, or an addition salt thereof with a pharmaceutically acceptable base, in combination with one or more pharmaceutically acceptable excipients.

7. A method for treating a human, afflicted with a condition selected from sleep disorders, major depression or seasonal affective disorder, insomnia and fatigue due to jetlag, comprising the step of administering to the human, a therapeutically effective amount of the compound of claim 1.

* * * * *